(12) United States Patent
Liu et al.

(10) Patent No.: US 9,488,560 B2
(45) Date of Patent: *Nov. 8, 2016

(54) DEVICE WITH POSITION-LIMIT SPRING FOR ALTERNATING TENSION-COMPRESSION CYCLIC TEST

(71) Applicant: Sichuan University, Chengdu (CN)

(72) Inventors: Jianfeng Liu, Chengdu (CN); Heping Xie, Chengdu (CN); Yang Ju, Chengdu (CN); Jianliang Pei, Chengdu (CN); Huining Xu, Chengdu (CN); Lu Wang, Chengdu (CN); Fei Wu, Chengdu (CN); Wenxi Fu, Chengdu (CN)

(73) Assignee: SICHUAN UNIVERSITY, Chengdu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/015,151

(22) Filed: Feb. 4, 2016

(65) Prior Publication Data

US 2016/0231215 A1 Aug. 11, 2016

(30) Foreign Application Priority Data

Feb. 9, 2015 (CN) .......................... 2015 1 0067094

(51) Int. Cl.
*G01N 3/08* (2006.01)
(52) U.S. Cl.
CPC ...................................... *G01N 3/08* (2013.01)

(58) Field of Classification Search
CPC ............. G01N 3/08; G01N 3/00; G01L 3/24
USPC .................. 73/826, 788, 796, 806, 760, 862
See application file for complete search history.

(56) References Cited

U.S. PATENT DOCUMENTS

| 2008/0276719 A1* | 11/2008 | Xu ........................... G01N 3/08 73/831 |
| 2009/0266548 A1* | 10/2009 | Olsen .................... E21B 49/006 166/308.1 |

\* cited by examiner

*Primary Examiner* — Lisa Caputo
*Assistant Examiner* — Nigel Plumb
(74) *Attorney, Agent, or Firm* — Matthias Scholl, PC; Matthias Scholl (57) ABSTRACT

A rock sample fixing device with position-limit spring components for cyclic tension and compression tests including: a lower clamp and an upper clamp; the lower clamp including a lower connector connected to a loading base at a bottom of a testing machine, a lower end cap for fixing samples, a lower chain connecting the lower connector and the lower end cap, a first central position-limit mechanism, a second central position-limit mechanism, and a first hydraulic mechanism; the upper clamp including an upper connector connected to a loading base at a top of the testing machine, an upper end cap for fixing samples, an upper chain connecting the upper connector and the upper end cap, a third central position-limit mechanism, a fourth central position-limit mechanism, and a second hydraulic mechanism.

3 Claims, 7 Drawing Sheets

DEVICE WITH POSITION-LIMIT SPRING FOR ALTERNATING TENSION-COMPRESSION CYCLIC TEST

CROSS-REFERENCE TO RELATED APPLICATIONS

Pursuant to 35 U.S.C. §119 and the Paris Convention Treaty, this application claims the foreign priority benefit of Chinese Patent Application No. 201510067094.9 filed Feb. 9, 2015, the contents of which, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, and Cambridge, Mass. 02142.

BACKGROUND OF THE INVENTION

1. Field of the Invention

The invention relates to a device used for conducting mechanical property tests on fragile materials, in particular to a device fixing rock samples in direct cyclic tension and compression tests for a testing machine.

2. Description of the Related Art

However, at present, due to structural limits of a sample fixing device, only a unidirectional compression test or a unidirectional tension measurement can be conducted in a rock test.

The unidirectional tension test still has the following shortcomings: (1) test results are not accurate; (2) it is easy to damage rock samples and not conducive to the test of the mechanical effect after rock test peak stress; and (3) it is not easy to operate and the labor intensity is relatively high.

In a unidirectional compression test, samples can only bear compression load but can't bear direct tension load. Therefore, a cyclic alternate compression and tension load test can't be conducted.

SUMMARY OF THE INVENTION

In view of the above-described problems, it is one objective of the invention to provide a rock sample fixing device with position-limit spring components for cyclic tension and compression tests so as to conduct cyclic alternate tension and compression load tests on rock samples, and ensure that the center line of the rock sample fixing device and the center line of the testing machine coincide in tests and the loading rigidity of the two sample ends is the same, which makes the connection of chains and end caps become easy, labor-saving and efficient.

To achieve the above objective, in accordance with one embodiment of the invention, there is provided a rock sample fixing device with position-limit spring components for cyclic tension and compression tests comprising a lower clamp and an upper clamp: the lower clamp consists of a lower connector connected to the loading base at the bottom of the testing machine, a lower end cap for fixing samples, a lower chain connecting the lower connector and the lower end cap, a first central position-limit mechanism, a second central position-limit mechanism and a first hydraulic mechanism, and the lower end cap consists of a first sample fixing groove and a first connection segment; and the upper clamp consists of an upper connector connected to the loading base at the top of the testing machine, an upper end cap for fixing samples, an upper chain connecting the upper connector and the upper end cap, a third central position-limit mechanism, a fourth central position-limit mechanism and a second hydraulic mechanism, and the upper end cap consists of a second sample fixing groove and a second connection segment; the first central position-limit mechanism, the second central position-limit mechanism, the third central position-limit mechanism and the fourth central position-limit mechanism have the same structure and all consist of position-limit spring components, a support and a connecting board; the position-limit spring component consists of a circular support base, three screws, three threaded inserts with male and female threads, three position-limit springs and three position-limit bodies. Three screw holes are arranged in the wall of the circular support base. The center lines of the three screw holes all pass through the center of the circular support base. The angle between the center lines of neighboring screw holes is 120°. The female threads of the three screw holes match the male threads of the threaded inserts. The female threads of the threaded inserts match the male threads of the screws. A screw hole is arranged on the position-limit body. The female thread of the screw hole matches the male thread of the screw. One end of the support is connected to the connecting board; and the other end of the support is connected to the circular support base of the position-limit spring component. The three threaded inserts are arranged in the three screw holes of the circular support base. The three screws are assembled with the three threaded inserts respectively. The three position-limit bodies are arranged on the three screws respectively. The three position-limit springs are arranged on the three screws respectively; one ends of the springs contact the position-limit bodies arranged on the screws; and the other ends of the springs contact the internal wall of the circular support base. The first hydraulic mechanism and the second hydraulic mechanism have the same structure, which both comprise a circular piston and a circular oil cylinder assembled with the circular piston. The first central position-limit mechanism and the loading base at the bottom of the testing machine are assembled. The circular support base of the position-limit spring component in the first central position-limit mechanism contacts the loading base at the bottom of the testing machine. The lower connector is arranged in the center hole of the circular support base. One ends of the three screws of the position-limit spring component in the first central position-limit mechanism contact the external side of the lower connector respectively. The second central position-limit mechanism and the lower end cap are assembled. The circular support base of the position-limit spring component in the second central position-limit mechanism contacts the outer bottom wall of the first sample fixing groove of the lower end cap. The first connection segment of the lower end cap is arranged in the center hole of the circular support base. One ends of the three screws of the position-limit spring component in the second central position-limit mechanism contact the external side of the lower end cap. The first hydraulic mechanism is arranged between the first central position-limit mechanism and the second central position-limit mechanism The circular oil cylinder of the first hydraulic mechanism is connected to the connecting board of the first central position-limit mechanism and the circular piston of the first hydraulic mechanism is connected to the connecting board of the second central position-limit mechanism; or, the circular oil cylinder of the first hydraulic mechanism is connected to the connecting board of the second central position-limit mechanism and the circular piston of the first hydraulic mechanism is connected to the connecting board of the first central position-limit mechanism. The lower chain is arranged in the space enclosed by the first central position-limit mechanism, the first hydraulic mechanism and the second central position-limit mechanism. The third central position-limit mechanism and the upper end cap are assembled. The circular support base of the position-limit spring component in the third central position-limit mechanism contacts the outer bottom wall of the second sample fixing groove of the upper end cap. The second connection segment of the upper end cap is arranged in the center hole of the circular support base. One ends of the three screws of the position-limit spring component in the third central position-limit mechanism contact the external side of the second connection segment of the upper end cap respectively. The fourth central position-limit mechanism and the loading base at the top of the testing machine are assembled. The circular support base of the position-limit spring component in the fourth central position-limit mechanism contacts the loading base at the top of the testing machine. The upper connector is arranged in the center hole of the circular support. One ends of the three screws of the position-limit spring component in the fourth central position-limit mechanism contact the outer side of the upper connector. The second hydraulic mechanism is arranged between the third central position-limit mechanism and the fourth central position-limit mechanism. The circular oil cylinder of the second hydraulic mechanism is connected to the connecting board of the third central position-limit mechanism and the circular piston of the second hydraulic mechanism is connected to the connecting board of the fourth central position-limit mechanism; or, the circular oil cylinder of the second hydraulic mechanism is connected to the connecting board of the fourth central position-limit mechanism and the circular piston of the second hydraulic mechanism is connected to the connecting board of the third central position-limit mechanism The upper chain is arranged in the space enclosed by the third central position-limit mechanism, the second hydraulic mechanism and the fourth central position-limit mechanism.

In a class of this embodiment, the supports in the first central position-limit mechanism, the second central position-limit mechanism, the third central position-limit mechanism and the fourth central position-limit mechanism are four round rods, the connecting board is a circular board, and the four round rods are all arranged on the circular support base and the circular surface of the connecting board; or, the supports in the first central position-limit mechanism, the second central position-limit mechanism, the third central position-limit mechanism and the fourth central position-limit mechanism are two board bodies with a circular arc cross section, the connecting board is a circular board, the two board bodies are arranged on the circular support base and the circular surface of the connecting board symmetrically.

Compared with existing technologies, advantages of the rock sample fixing device with position-limit spring components for cyclic tension and compression tests are as follows:

1. Hydraulic mechanisms are arranged on the rock sample fixing device hereof to replace compression spiral springs. Since the pressure and rigidity provided by hydraulic mechanisms are much higher than the pressure and rigidity provided by spiral springs, the invention can conduct cyclic alternate tension and compression load tests on rock samples and has overcome the shortcoming that only a unidirectional compression or tension test can be conducted in current rock tests, and improved the combined test method for conducting cyclic alternate direct tension and compression load tests on unidirectional loading rock samples.

2. Since two central position-limit mechanisms and one hydraulic mechanism are arranged on both the lower clamp and the upper clamp of the rock sample fixing device hereof, the invention can not only ensure that the loading rigidity at both ends of a sample in a test are consistent but also test the mechanical effect after rock test peak stress more effectively. Through the position-limit spring components in the central position-limit mechanisms of the lower clamp and the upper clamp, the invention can ensure that the center line of the rock sample fixing device and the center line of the testing machine coincide in the test, avoid the occurrence of additional eccentric force and be conducive to improvement of accuracy of test results.

3. Since the supports of the first central position-limit mechanism, the second central position-limit mechanism, the third central position-limit mechanism and the fourth central position-limit mechanism are four round rods or two board bodies with a circular arc cross section, it is easy to insert the supports into connector bolts, and install and dismantle the supports when the chains are connected to the end caps. And, at the same time, it is conducive to protecting the integrity of rock samples with low tensile strength before a test so as to improve the success rate of the test.

In figures, the following reference numbers are used: 1. Loading base at a bottom of a testing machine; 2. Position-limit spring component; 2-1. Circular support base; 2-2. Screw; 2-3. Threaded insert; 2-4. Position-limit spring; 2-5. Position-limit body; 3. Lower connector; 4. Support; 5. Connecting board; 6. Lower chain; 7. Lower bolt; 8. Lower end cap; 9. Rock sample; 10. Upper end cap; 11. Upper bolt; 12. Upper chain; 13. Upper connecter; 14. Loading base at a top of the testing machine; 15. Circular piston; 16. Circular oil cylinder; 17. Piston position-limit ring; 18. Sealing washer; 19. Oil pipe; 20. Control valve; 21. Pressure gage; 100. First central position-limit mechanism; 200. Second central position-limit mechanism; 300. Third central position-limit mechanism; and 400. Fourth central position-limit mechanism.

DETAILED DESCRIPTION OF THE EMBODIMENTS

For further illustrating the invention, experiments detailing a rock sample fixing device with position-limit spring components for cyclic tension and compression tests are described below. It should be noted that the following examples are intended to describe and not to limit the invention.

Figure 1:
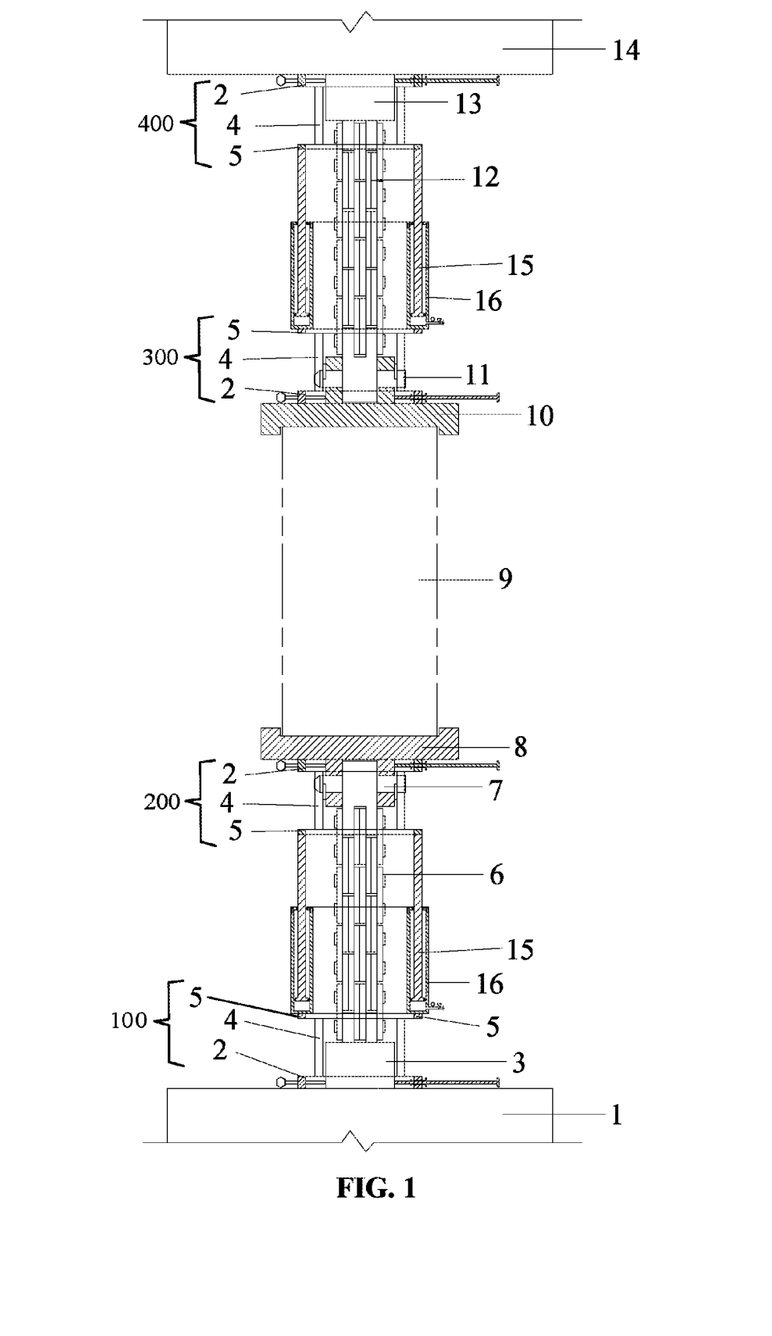
FIG. 1 is a schematic diagram of a rock sample fixing device with position-limit spring components for cyclic tension and compression tests in accordance with one embodiment of the invention.

In the embodiment, the rock sample fixing device with position-limit spring components for cyclic tension and compression tests consists of a lower clamp and an upper clamp as shown in the FIG. 1. The lower clamp consists of a lower connector 3 connected to the loading base 1 at the bottom of the testing machine, a lower end cap 8 for fixing samples, a lower chain 6 connecting the lower connector and the lower end cap, a first central position-limit mechanism 100, a second central position-limit mechanism 200 and a first hydraulic mechanism, and the lower end cap 8 consists of a first sample fixing groove and a first connection segment; and the upper clamp consists of an upper connector 13 connected to the loading base 14 at the top of the testing machine, an upper end cap 10 for fixing samples, an upper chain 12 connecting with the upper connector and the upper end cap, a third central position-limit mechanism 300, a fourth central position-limit mechanism 400 and a second hydraulic mechanism, and the upper end cap 10 consists of a second sample fixing groove and a second connection segment.

Figure 2:
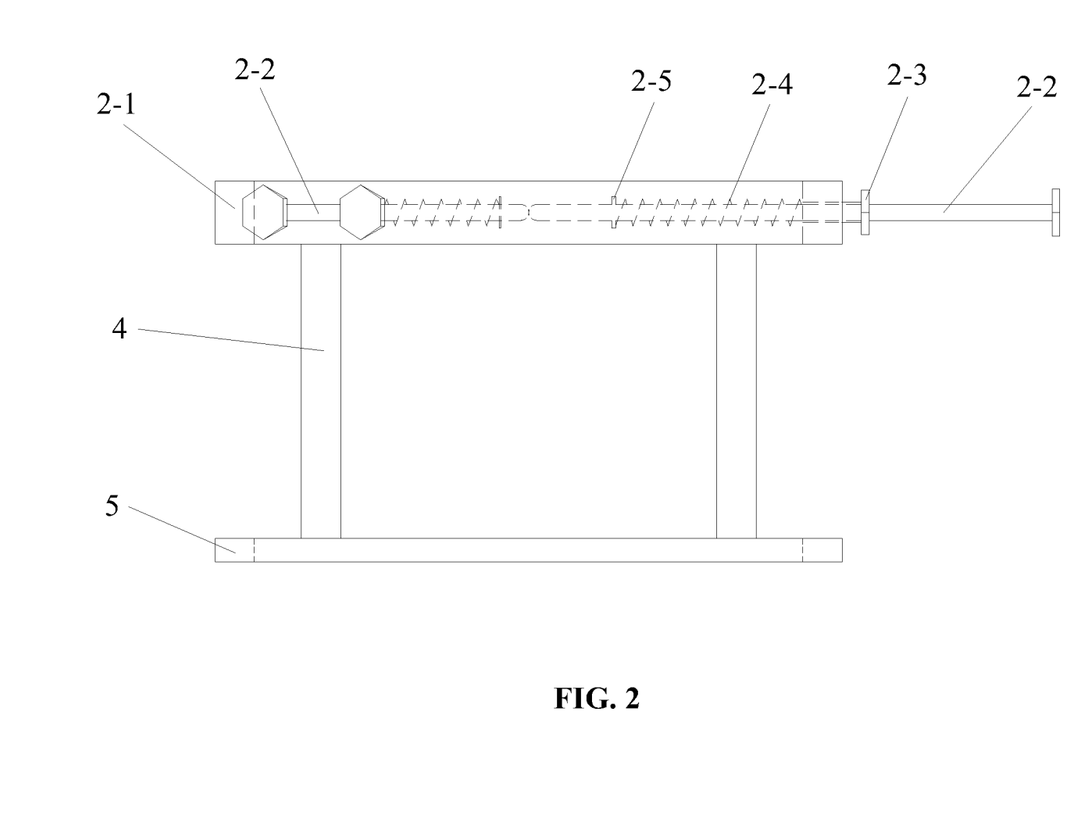
FIG. 2 is a first schematic diagram of a first central position-limit mechanism or a second central position-limit mechanism or a third central position-limit mechanism or a fourth central position-limit mechanism in a rock sample fixing device with position-limit spring components for cyclic tension and compression tests (supports are round rods) in accordance with one embodiment of the invention; the central position-limit mechanism is in a non-working state.
Figure 3:
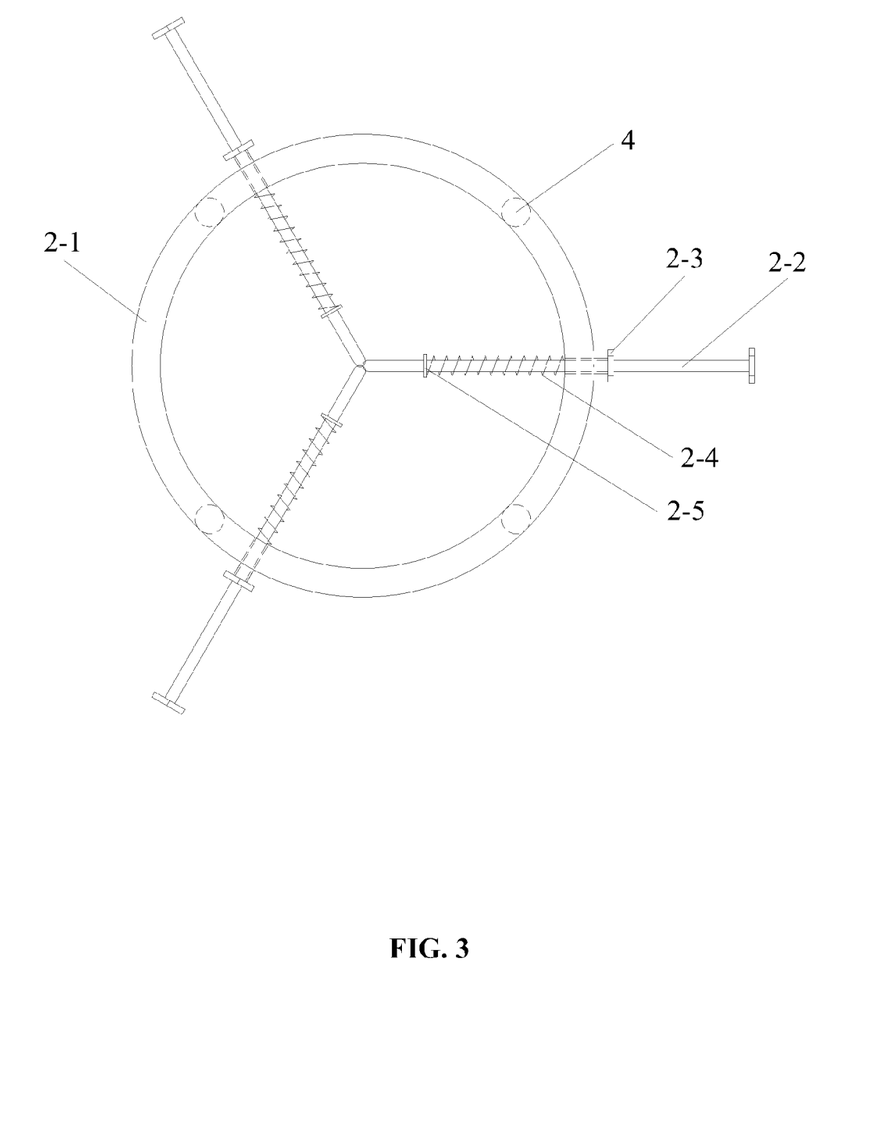
FIG. 3 is a top view of a central position-limit mechanism of a rock sample fixing device with position-limit spring components for cyclic tension and compression tests in FIG. 2 in accordance with one embodiment of the invention.

The first central position-limit mechanism 100, the second central position-limit mechanism 200, the third central position-limit mechanism 300 and the fourth central position-limit mechanism 400 have the same structure and all consist of position-limit spring components 2, a support 4 and a connecting board 5 as shown in FIGS. 2-3. The position-limit spring component 2 consists of a circular support base 2-1, three screws 2-2, three threaded inserts 2-3 with male and female threads, three position-limit springs 2-4 and three position-limit bodies 2-5. Three screw holes are arranged in the wall of the circular support base. The center lines of the three screw holes all pass through the center of the circular support base. The angle between the center lines of neighboring screw holes is 120°. The female threads of the three screw holes match the male threads of the threaded inserts 2-3. The female threads of the threaded inserts 2-3 match the male threads of the screws 2-2. The position-limit bodies 2-5 are nuts matching the male threads of the screws 2-2. The position-limit springs 2-4 are column compression spiral springs. The supports 4 are four round rods. The connecting board 5 is a circular board, whose outer diameter and inner hole diameter are identical with the outer diameter and inner hole diameter of the circular support base 2-1. The four round rods are all arranged on the circular support base 2-1 and the circular surface of the connecting board 5; and one ends of the round rods are connected to the circular support base 2-1. The three threaded inserts 2-3 are respectively arranged in the three screw holes of the circular support base. The three screws 2-2 are assembled with the three threaded inserts respectively. The three position-limit bodies 2-5 are arranged on the three screws respectively. The three position-limit springs 2-4 are arranged on the three screws respectively; one ends of the springs contact the position-limit bodies 2-5 arranged on the screws; and the other ends of the springs contact the internal wall of the circular support base 2-1.

Figure 6:
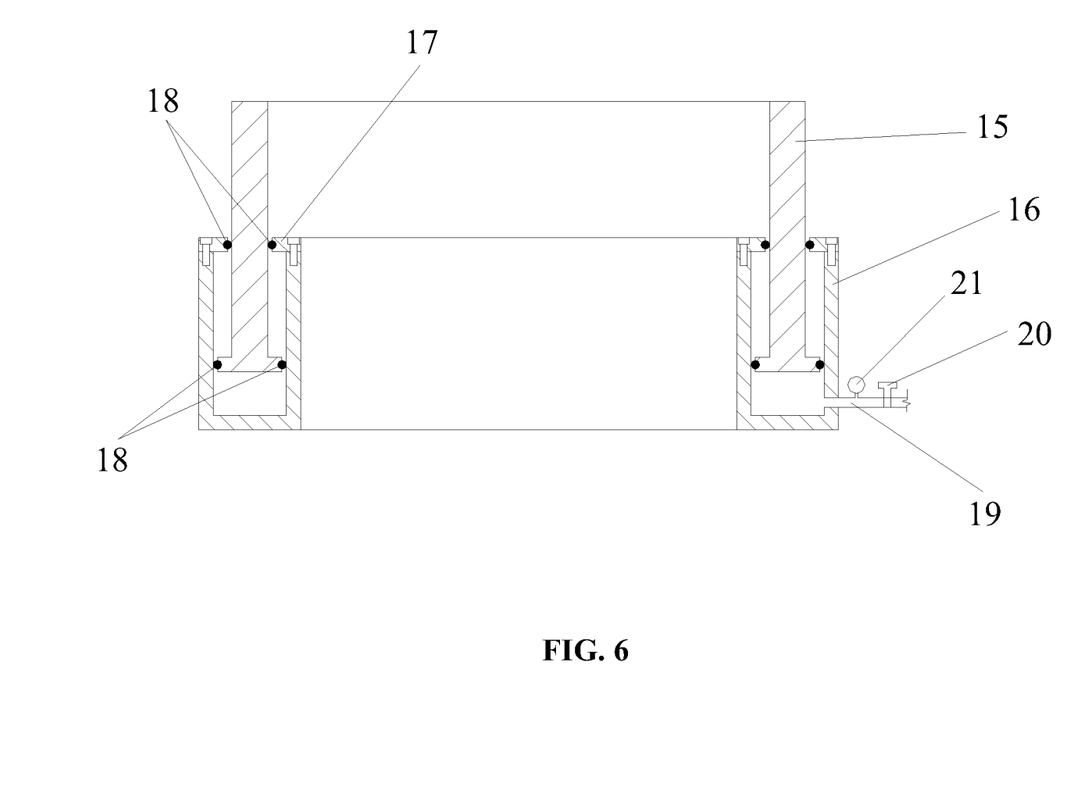
FIG. 6 is a schematic diagram of a first hydraulic mechanism in a rock sample fixing device with position-limit spring components for cyclic tension and compression tests or the second hydraulic mechanism in accordance with one embodiment of the invention.
Figure 7:
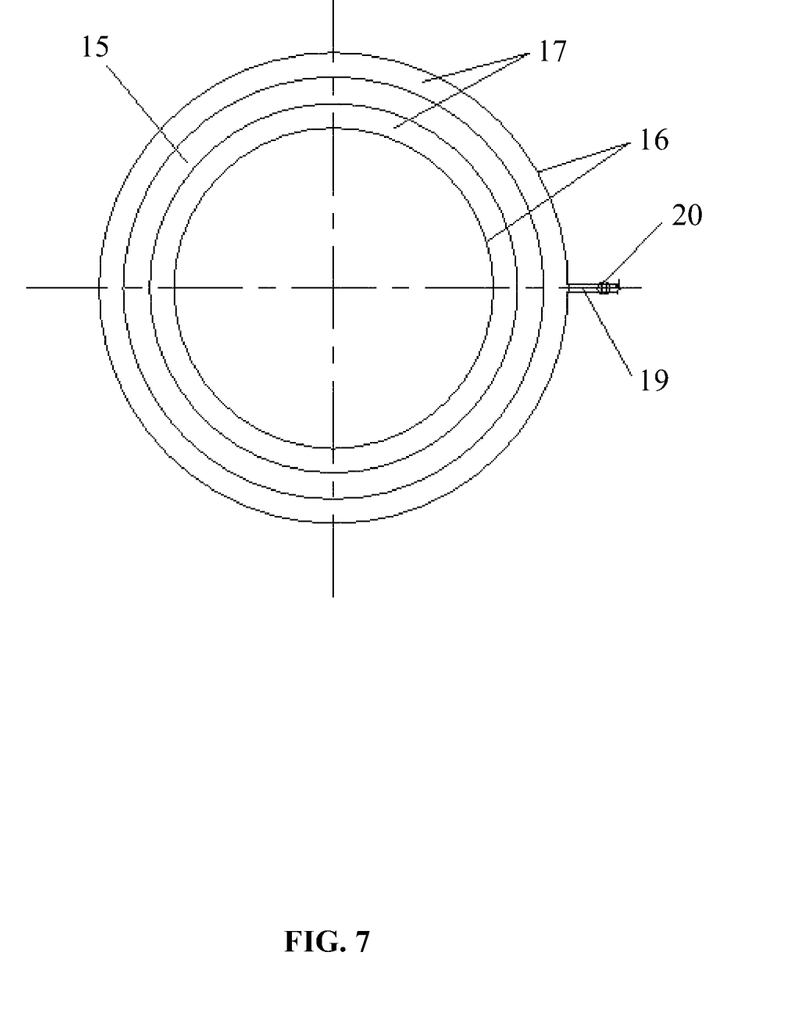
FIG. 7 is top view of a first hydraulic mechanism or a second hydraulic mechanism in FIG. 6 in accordance with one embodiment of the invention.

As shown in FIGS. 6-7, the first hydraulic mechanism and the second hydraulic mechanism both comprise a circular piston 15, a circular oil cylinder 16, a piston position-limit ring 17 and sealing washers 18. One end of the circular piston 15 is inserted into and arranged in the circular cavity of the circular oil cylinder 16. An oil pipe 19 connected to the cavity is arranged at the closed end of the circular cavity of the circular oil cylinder 16. A control valve 20 and a pressure gauge 21 are arranged on the oil pipe 19. The piston position-limit ring 17 is arranged on the open end of the circular cavity of the circular oil cylinder 16. The sealing washers 18 are arranged on one end of the circular cavity inserted into the circular piston 15 and on the piston position-limit ring 17.

The assembly method of each member or component of the lower clamp: the first central position-limit mechanism 100 and the loading base 1 at the bottom of the testing machine are assembled. The circular support base of the position-limit spring component contacts the loading base 1. The lower connector 3 is arranged in the center hole of the circular support base. One ends of the three screws of the position-limit spring component in the first central position-limit mechanism 100 contact the external side of the lower connector 3 respectively. The second central position-limit mechanism 200 and the lower end cap 8 are assembled. The circular support base of the position-limit spring component in the second central position-limit mechanism 200 contacts the outer bottom wall of the first sample fixing groove of the lower end cap 8. The first connection segment of the lower end cap 8 is arranged in the center hole of the circular support base. One ends of the three screws of the position-limit spring component in the second central position-limit mechanism 200 contact the external side of the lower end cap. The first hydraulic mechanism is arranged between the first central position-limit mechanism 100 and the second central position-limit mechanism 200. The circular oil cylinder 16 of the first hydraulic mechanism is connected to the connecting board 5 of the first central position-limit mechanism 100 and the circular piston 15 of the first hydraulic mechanism is connected to the connecting board 5 of the second central position-limit mechanism 200. The lower end of the lower chain 6 is connected to the lower connector 3 arranged on the loading base 1 at the bottom of the testing machine; and a dismountable connection between the upper end of the lower chain and the lower end cap is formed by the bolt 7. The lower chain 6 is arranged in the space enclosed by the first central position-limit mechanism 100, the first hydraulic mechanism and the second central position-limit mechanism 200.

The assembly method of each member or component of the upper clamp: the third central position-limit mechanism 300 and the upper end cap 10 are assembled. The circular support base of the position-limit spring component in the third central position-limit mechanism 300 contacts the outer bottom wall of the second sample fixing groove of the upper end cap 10. The second connection segment of the upper end cap 10 is arranged in the center hole of the circular support base. One ends of the three screws of the position-limit spring component in the third central position-limit mechanism 300 respectively contact the external side of the second connection segment of the upper end cap. The fourth central position-limit mechanism 400 and the loading base 14 at the top of the testing machine are assembled. The circular support base of the position-limit spring component in the fourth central position-limit mechanism 400 contacts the loading base 14 at the top of the testing machine. The upper connector 13 is arranged in the center hole of the circular support. One ends of the three screws of the position-limit spring component in the fourth central position-limit mechanism 400 respectively contact the outer side of the upper connector 13. The second hydraulic mechanism is arranged between the third central position-limit mechanism 300 and the fourth central position-limit mechanism 400. The circular oil cylinder 16 of the second hydraulic mechanism is connected to the connecting board 5 of the third central position-limit mechanism 300 and the circular piston 15 of the second hydraulic mechanism is connected to the connecting board 5 of the fourth central position-limit mechanism 400. The upper end of the upper chain 12 is connected to the upper connector 13 arranged on the loading base 14 at the top of the testing machine; a dismountable connection between the lower end of the upper chain and the upper end cap is formed by the bolt 11. The upper chain 12 is arranged in the space enclosed by the third central position-limit mechanism 300, the second hydraulic mechanism and the fourth central position-limit mechanism 400.

The rock sample 9 is arranged as shown in the FIG. 1. Both ends of the rock sample are connected to the second sample fixing grooves of the upper end cap 10 and the lower end cap 8 by high-strength adhesive.

It needs to be noted that the installation methods of screws 2-2, threaded inserts 2-3, position-limit springs 2-4 and position-limit bodies 2-5 in the position-limit spring component 2 are as follows: firstly, three threaded inserts 2-3 and three screws 2-2 are assembled; then the three screws 2-2 are inserted into the three screw holes of the circular support base 2-1 respectively; the three position-limit spring 2-4 are respectively sleeved with the segment in the center hole of the circular support base where the three screws are arranged; the three position-limit bodies 2-5 are respectively arranged on the segment in the center hole of the circular support base where the three screws are arranged. Through the adjustment of the three position-limit bodies, the three position-limit bodies are arranged in the positions equidistant from the end of the segment in the circular body where the three screws are arranged. The three position-limit springs are in the same compression state. And then the three screws are arranged on the circular support base by three threaded inserts.

Figure 4:
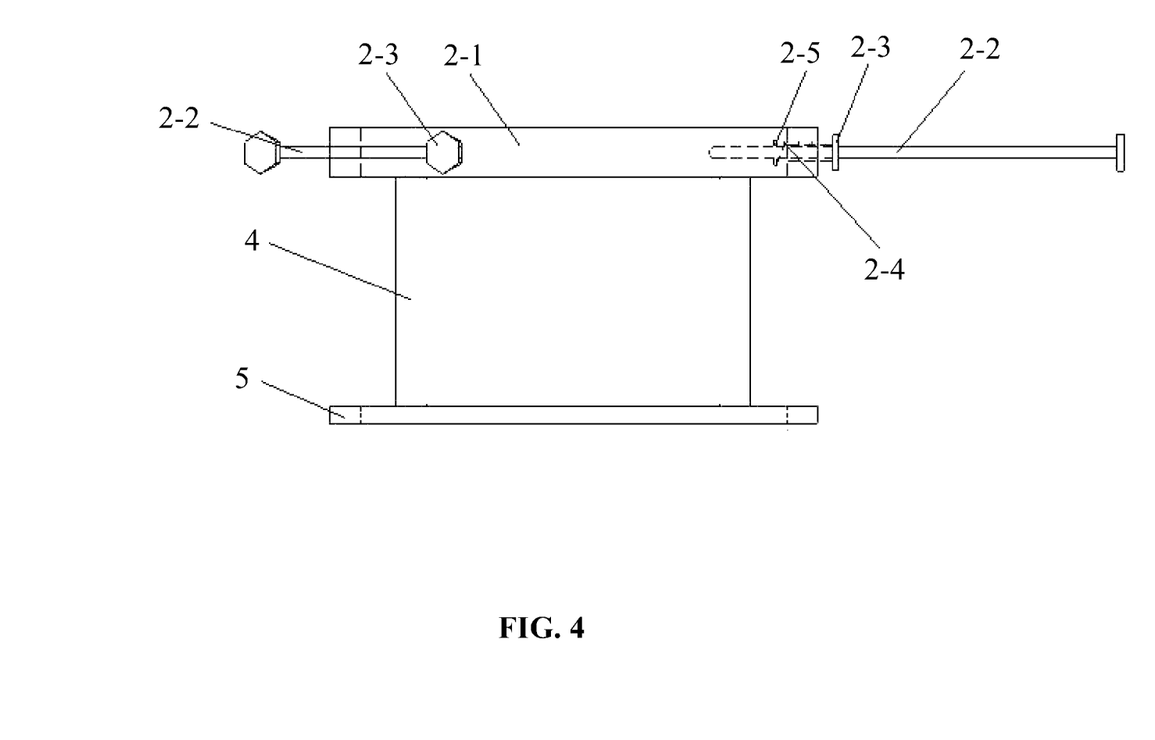
FIG. 4 is a second schematic diagram of a first central position-limit mechanism or a second central position-limit mechanism or a third central position-limit mechanism or a fourth central position-limit mechanism in a rock sample fixing device with position-limit spring components for cyclic tension and compression tests (the supports are arc board bodies) in accordance with one embodiment of the invention; the central position-limit mechanism is in a working state.
Figure 5:
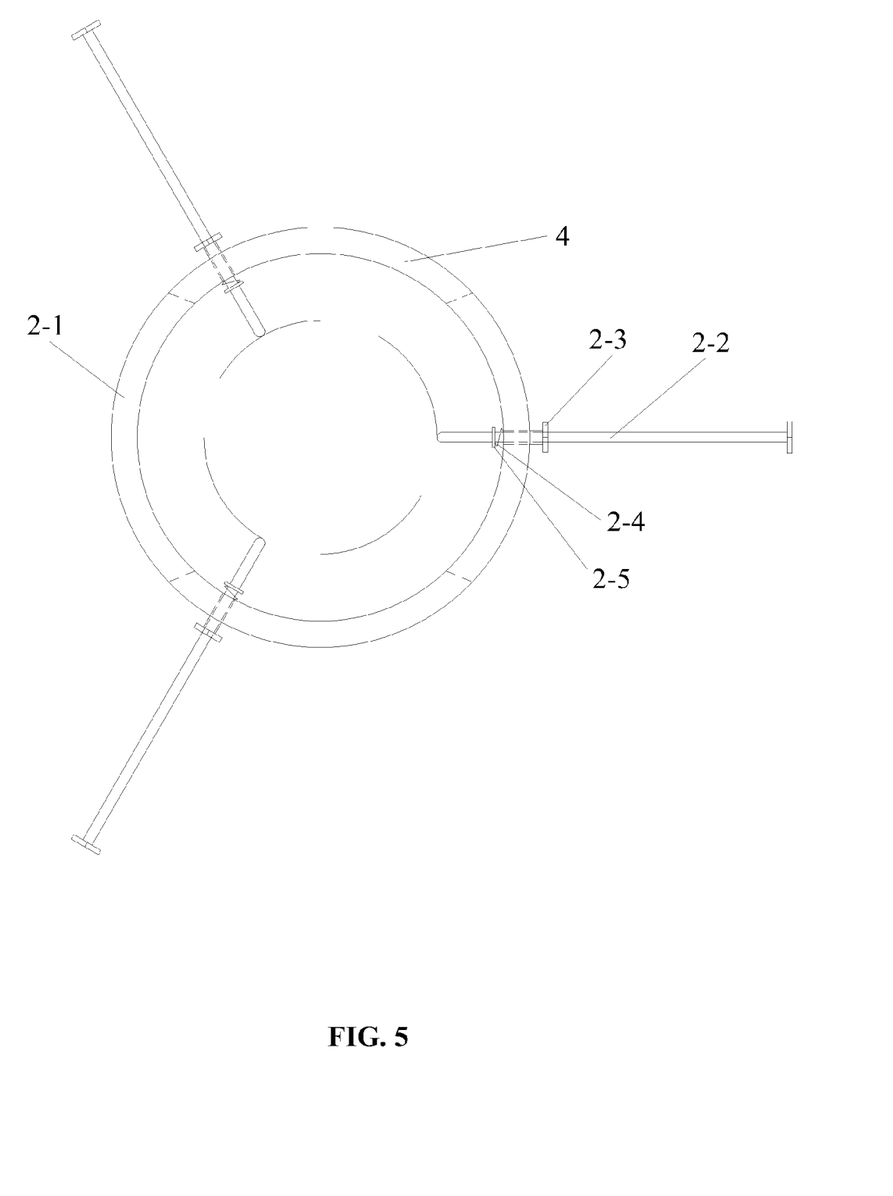
FIG. 5 is a top view of a central position-limit mechanism of a rock sample fixing device with position-limit spring components for cyclic tension and compression tests in FIG. 4 in accordance with one embodiment of the invention.

The invention is not limited to the embodiment. For example, the first central position-limit mechanism 100, the second central position-limit mechanism 200, the third central position-limit mechanism 300 and the fourth central position-limit mechanism 400 can also have the structure shown in FIGS. 4-5. That is, the supports 4 are two board bodies with a circular arc cross section; the connecting board 5 is a circular arc board; the two board bodies are arranged on the circular support base 2-1 and the circular surface of the connecting board 5 symmetrically; one ends of the two board bodies are connected to the connecting board 5; the other ends of the two board bodies are connected to the circular support base 2-1 in the position-limit spring component.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A rock sample fixing device with position-limit spring components for cyclic tension and compression tests, comprising:
   a lower clamp; the lower clamp comprising: a lower connector connected to a loading base at a bottom of a testing machine, a lower end cap for fixing samples comprising a first sample fixing groove and a first connection segment, a lower chain connecting the lower connector and the lower end cap, a first central position-limit mechanism, a second central position-limit mechanism, and a first hydraulic mechanism; and
   an upper clamp; the upper clamp comprising: an upper connector connected to a loading base at a top of the testing machine, an upper end cap for fixing samples comprising a second sample fixing groove and a second connection segment, an upper chain connecting the upper connector and the upper end cap, a third central position-limit mechanism, a fourth central position-limit mechanism, and a second hydraulic mechanism;
   wherein
   the first central position-limit mechanism, the second central position-limit mechanism, the third central position-limit mechanism and the fourth central position-limit mechanism have the same structure and all comprise position-limit spring components, a support and a connecting board; the position-limit spring component comprises a circular support base, three screws, three threaded inserts with male and female threads, three position-limit springs and three position-limit bodies; three screw holes are arranged in a wall of the circular support base; center lines of the three screw holes all pass through a center of the circular support base; an angle between the center lines of neighboring screw holes is 120°;the female threads of the three screw holes match with the male threads of the threaded inserts; the female threads of the threaded inserts match with the male threads of the screws; a screw hole is arranged on the position-limit body; the female thread of the screw hole matches with the male thread of the screw; one end of the support is connected to the connecting board; and another end of the support is connected to the circular support base of the position-limit spring component; the three threaded inserts are arranged in the three screw holes of the circular support base; the three screws are assembled with the three threaded inserts respectively; the three position-limit bodies are arranged on the three screws respectively; the three position-limit springs are arranged on the three screws respectively; one ends of the springs contact the position-limit bodies arranged on the screws; and another ends of the springs contact an internal wall of the circular support base;
   the first hydraulic mechanism and the second hydraulic mechanism have the same structure, which both comprise a circular piston and a circular oil cylinder assembled with the circular piston;

the first central position-limit mechanism and the loading base at the bottom of the testing machine are assembled; the circular support base of the position-limit spring component in the first central position-limit mechanism contacts the loading base at the bottom of the testing machine; the lower connector is arranged in a center hole of the circular support base; one ends of the three screws of the position-limit spring component in the first central position-limit mechanism contact the external side of the lower connector respectively; the second central position-limit mechanism and the lower end cap are assembled; the circular support base of the position-limit spring component in the second central position-limit mechanism contacts an outer bottom wall of the first sample fixing groove of the lower end cap; the first connection segment of the lower end cap is arranged in the center hole of the circular support base; one ends of the three screws of the position-limit spring component in the second central position-limit mechanism contact an external side of the lower end cap; the first hydraulic mechanism is arranged between the first central position-limit mechanism and the second central position-limit mechanism; the circular oil cylinder of the first hydraulic mechanism is connected to the connecting board of the first central position-limit mechanism and the circular piston of the first hydraulic mechanism is connected to the connecting board of the second central position-limit mechanism; or, the circular oil cylinder of the first hydraulic mechanism is connected to the connecting board of the second central position-limit mechanism and the circular piston of the first hydraulic mechanism is connected to the connecting board of the first central position-limit mechanism; the lower chain is arranged in a space enclosed by the first central position-limit mechanism, the first hydraulic mechanism and the second central position-limit mechanism;

the third central position-limit mechanism and the upper end cap are assembled; the circular support base of the position-limit spring component in the third central position-limit mechanism contacts the outer bottom wall of the second sample fixing groove of the upper end cap; the second connection segment of the upper end cap is arranged in the center hole of the circular support base; one ends of the three screws of the position-limit spring component in the third central position-limit mechanism contact the external side of the second connection segment of the upper end cap respectively; the fourth central position-limit mechanism and the loading base at the top of the testing machine are assembled; the circular support base of the position-limit spring component in the fourth central position-limit mechanism contacts the loading base at the top of the testing machine; the upper connector is arranged in the center hole of the circular support; one ends of the three screws of the position-limit spring component in the fourth central position-limit mechanism contact the outer side of the upper connector;

the second hydraulic mechanism is arranged between the third central position-limit mechanism and the fourth central position-limit mechanism; the circular oil cylinder of the second hydraulic mechanism is connected to the connecting board of the third central position-limit mechanism and the circular piston of the second hydraulic mechanism is connected to the connecting board of the fourth central position-limit mechanism; or, the circular oil cylinder of the second hydraulic mechanism is connected to the connecting board of the fourth central position-limit mechanism and the circular piston of the second hydraulic mechanism is connected to the connecting board of the third central position-limit mechanism; the upper chain is arranged in a space enclosed by the third central position-limit mechanism, the second hydraulic mechanism and the fourth central position-limit mechanism.

2. The device of claim 1, wherein the supports in the first central position-limit mechanism, the second central position-limit mechanism, the third central position-limit mechanism and the fourth central position-limit mechanism are four round rods, the connecting board is a circular board, and the four round rods are all arranged on the circular support base and a circular surface of the connecting board.

3. The device of claim 1, wherein the supports in the first central position-limit mechanism, the second central position-limit mechanism, the third central position-limit mechanism and the fourth central position-limit mechanism are two board bodies with a circular arc cross section, the connecting board is a circular board, the two board bodies are arranged on the circular support base and a circular surface of the connecting board symmetrically.

* * * * *